US009358307B2

(12) United States Patent
Pitcovski et al.

(10) Patent No.: US 9,358,307 B2
(45) Date of Patent: Jun. 7, 2016

(54) TARGETING OF INNATE IMMUNE RESPONSE TO TUMOR SITE

(75) Inventors: Jacob Pitcovski, Korazim (IL); Ehud Shahar, Kiryat Shmona (IL); Raphael Gorodetsky, Jerusalem (IL)

(73) Assignees: GAVISH-GALILEE BIO APPLICATIONS LTD., Kiryat Shmona (IL); HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 1265 days.

(21) Appl. No.: 12/864,550

(22) PCT Filed: Jan. 25, 2009

(86) PCT No.: PCT/IL2009/000097
§ 371 (c)(1),
(2), (4) Date: Jan. 24, 2011

(87) PCT Pub. No.: WO2009/093250
PCT Pub. Date: Jul. 30, 2009

(65) Prior Publication Data
US 2011/0123629 A1 May 26, 2011

Related U.S. Application Data

(60) Provisional application No. 61/006,659, filed on Jan. 25, 2008.

(51) Int. Cl.
*A61K 39/00* (2006.01)
*A61K 39/385* (2006.01)
*A61K 39/38* (2006.01)
*A61K 9/16* (2006.01)
*A61K 9/50* (2006.01)
*A61K 47/48* (2006.01)

(52) U.S. Cl.
CPC ......... *A61K 47/48853* (2013.01); *A61K 47/484* (2013.01); *A61K 47/48584* (2013.01); *A61K 39/00* (2013.01); *A61K 39/38* (2013.01); *A61K 39/385* (2013.01)

(58) Field of Classification Search
CPC .................... A61K 2300/00; A61K 47/48561; A61K 47/48884; A61K 39/395; A61K 2039/505; A61K 39/39558; A61K 49/0093; A61K 49/0058; A61K 49/1833; A61K 49/225; A61K 51/1244; A61K 9/127
See application file for complete search history.

(56) References Cited

U.S. PATENT DOCUMENTS

| 6,410,517 | B1 | 6/2002 | Truong et al. |
|---|---|---|---|
| 6,676,941 | B2 * | 1/2004 | Thorpe et al. ............. 424/178.1 |
| 2004/0110239 | A1 | 6/2004 | Bussolati et al. |
| 2005/0053667 | A1 * | 3/2005 | Irvine et al. .................. 424/490 |
| 2005/0214286 | A1 * | 9/2005 | Epstein et al. ............. 424/144.1 |
| 2006/0002852 | A1 | 1/2006 | Saltzman et al. |
| 2009/0148535 | A1 * | 6/2009 | Bamdad ........................ 424/499 |
| 2010/0098632 | A1 | 4/2010 | Russell et al. |
| 2010/0104503 | A1 | 4/2010 | Mellman et al. |
| 2010/0135976 | A1 * | 6/2010 | Nilsson et al. ............. 424/93.73 |
| 2010/0151031 | A1 | 6/2010 | Desimone et al. |
| 2010/0166751 | A1 * | 7/2010 | Ostroff et al. ............. 424/133.1 |
| 2012/0309029 | A1 * | 12/2012 | Fantl et al. .................. 435/7.23 |

FOREIGN PATENT DOCUMENTS

| EP | 1 357 132 A2 | 10/2003 |
|---|---|---|
| EP | 1952825 | * 10/2006 |
| EP | 1 952 825 A1 | 8/2008 |
| WO | WO 97/31655 | * 9/1997 |
| WO | WO9731655 A2 | 9/1997 |
| WO | WO03070909 A2 | 8/2003 |
| WO | WO2005072088 A2 | 8/2005 |
| WO | WO2007048326 A1 | 5/2007 |
| WO | WO2008008917 A2 | 1/2008 |
| WO | WO2008115641 A2 | 9/2008 |
| WO | WO2008118861 A2 | 10/2008 |

OTHER PUBLICATIONS

Zhang et al., Clinical Pharmacology and Therapeutics, Oct. 24, 2007.*
Baselga et al., Annals of Oncology, 2001; 12(Suppl 1): S35-S41.*
Dresco et al., Langmuir, 1999; 15: 1945-1951.*
Jeong et al., J. Am. Chem. Soc., 2005; 127: 1098-1099.*
Celis, Cancer Res, 2007; 67(17): 7945-7.*
Zhang et al., "Nanoparticles in Medicine: Therapeutic Applications and Developments" Clin Pharmacol Ther; vol. 83 (5) pp. 761-769 (2008).
Kaptain et al., "Her-2/neu and Breast Cancer" Diagn Mol Pathol; vol. 10 (3) pp. 139-152 (2001).
Cheung et al., "Tumour marker measurements in the diagnosis and monitoring of breast cancer" Cancer Treat Rev; vol. 26 pp. 91-102 (2000).
Reichert et al., "Development trends for monoclonal antibody cancer therapeutics" Nat Rev Drug Discov; vol. 6 pp. 349-356 (2007).
Wang et al., "Toll-like receptors and immune regulation: implications for cancer therapy" Oncogene; vol. 27 pp. 181-189 (2008).
Scheel et al. "Therapeutic anti-tumor immunity triggered by injections of immunostimulating single-stranded RNA" Eur J Immunol; vol. 36 pp. 2807-2816 (2006).

(Continued)

Primary Examiner — Gary Nickol
Assistant Examiner — Lakia Tongue
(74) Attorney, Agent, or Firm — Browdy and Neimark, PLLC

(57) ABSTRACT

The invention provides microparticles or nanoparticles for treatment of tumors comprising: (i) a targeting agent to the tumor or the tumor environment; and (ii) at least one inducer that stimulates a desired immune response in the tumor environment, leading to tumor apoptosis, wherein components (i) and (ii) are non-covalently or covalently attached to the surface of said microparticles or nanoparticles. The targeting agent is an agent that recognizes and binds to an antigen, a receptor or other molecules found on the surface of tumor cells or in the tumor environment and are preferably antibodies.

20 Claims, 13 Drawing Sheets
(12 of 13 Drawing Sheet(s) Filed in Color)

(56) References Cited

OTHER PUBLICATIONS

Salaun et al., "TLR3 Can Directly Trigger Apoptosis in Human Cancer Cells" J Immunol; vol. 176 pp. 4894-4901 (2006).

Sfondrini et al., "Antitumor Activity of the TLR-5 Ligand Flagellin in Mouse Models of Cancer" J Immunol vol. 176 pp. 6624-6630 (2006).

O'Hagan et al., "Microparticle-based technologies for vaccines" Methods; vol. 40 pp. 10-19 (2006).

http://www.sciencedaily.com/releases/2007/04/070418110944.htm "Boosting Immune 'Killer Cells,' Increases Antibody Effectiveness Against Cancer" [internet] Downloaded: Apr. 19, 2007.

Gøril Berntzen et al; "The Tumor Necrosis Factor-Inducing Potency of Lipopolysaccharide and Uronic Acid Polymers Is Increased when They Are Covalently Linked to Particles" Clinical and Diagnostic Laboratory Immunology p. 355-361, vol. 5, No. 3 (1998).

* cited by examiner

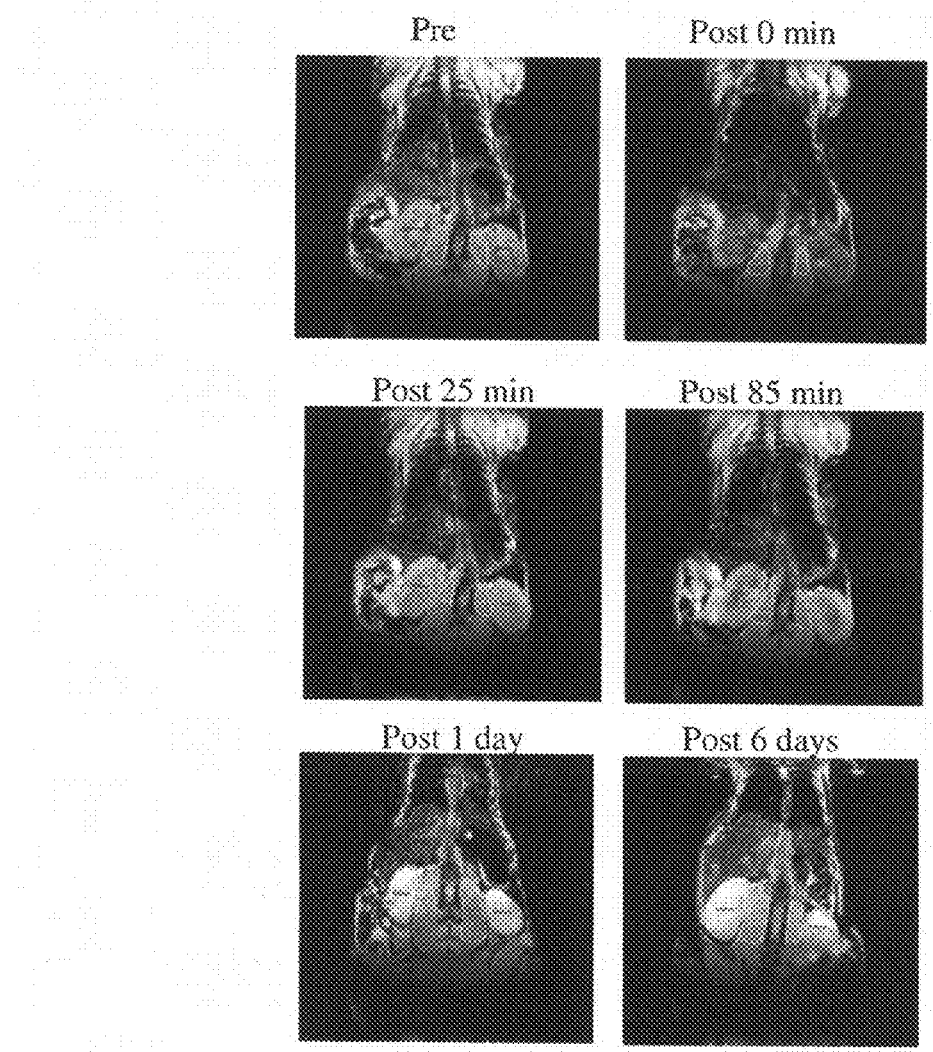

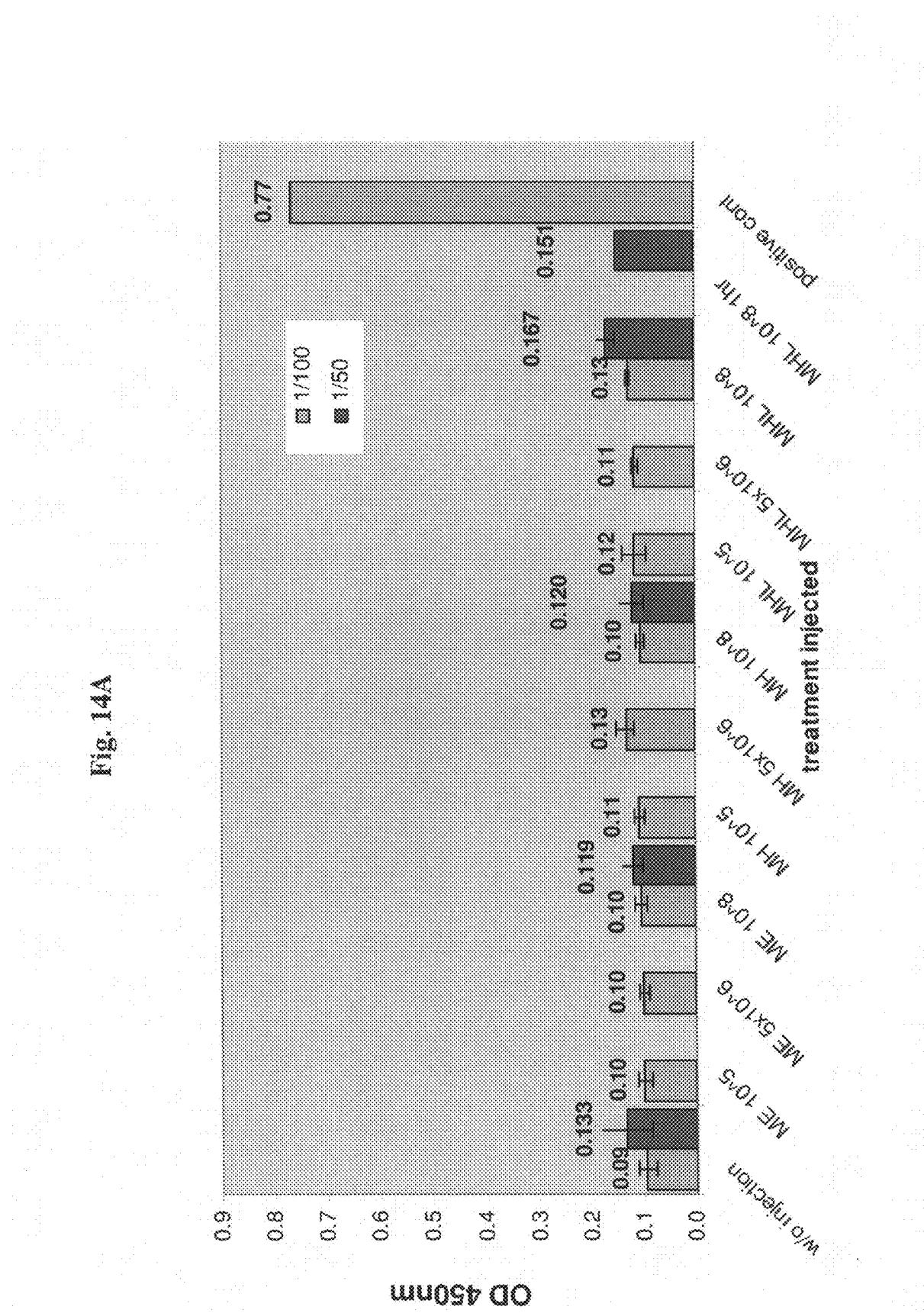

TARGETING OF INNATE IMMUNE RESPONSE TO TUMOR SITE

FIELD OF THE INVENTION

The present invention is in the field of Immunology and relates to microparticles and nanoparticles and compositions comprising an agent for targeting to malignant tumors and an agent that triggers specific immune cells to cause apoptosis of the tumors. Specifically, the current invention relates to particles carrying a tumor-targeting component and an inducer that stimulates a local immune response aimed at tumor elimination.

BACKGROUND OF THE INVENTION

Tumor specific or over-expressed antigens were detected on the surface of various cancer cells. e.g. HER2, specific MUC I, GM2 and MHC class II on melanoma cells. These and other markers may be used to target tumors, using specific antibodies, for example. Antibodies against tumor antigens were developed and are used in immunotherapy. Binding of antibodies to tumor, native or as carriers of various toxins may damage the tumor cells. Nevertheless, the number of cells in solid tumors is huge, and continue to proliferate and adjust to the treatment during the period of the treatment.

Innate immune responses may affect tumor mass, but in most cases they do not eliminate the progression of solid tumors. Recruiting specific immune cells and controlling desired responses could be performed by defined inducers. Macrophages maturate from monocytes and migrate to tissues, e.g. digestive tract, lung, blood vessels, liver. Neutrophils (polymorphonuclear cells) are present in the blood but not in normal tissues. Mostly, these cells of the innate immune system overcome infections, without help of the acquired arm. Macrophages arrive at the site of infection and attract large amounts of neutrophils. Both cell types identify pathogens through receptors which recognize molecules that are common to various alien pathogens. One of the major differences between pathogenic and non-pathogenic microorganisms is their ability to outperform the innate immune system. This is done in part of the cases by using polysaccharide capsules that mask the pathogen and is not identified by any of the macrophage receptors.

Receptors on different cells of the innate immune system allow fast response (hours) to pathogen (contrary to acquired immune response that takes days to develop). These receptors enable a diverse response. Some identify repeated structural motifs on the surface of pathogen, e.g. mannose receptor on macrophages. (but not monocytes or neutrophils), CD14 receptor to LPS and CD11/CD18 to glucan. A second type of receptors is characteristic of the complement and Fc of antibodies. These receptors allow identification and engulfment of particles that were detected and attached in sera to complement or antibodies. In addition there are receptors that induce movement towards a specific site (chemotaxis), e.g. f-Met-Leu-Phe bind to peptides N-formylated that are produced by bacteria. Another group of receptors induce effector molecules and influence the nature of the response, including concentration and activation of cells in the infected area.

An important factor in the macrophage-pathogen interaction is the release of cytokines that attract neutrophils and plasma proteins to initiate the inflammation process. Receptors that tag for the presence of a pathogen and stimulate expression of co-stimulatory molecules on macrophages and dendritic cells also stimulate the acquired immune response, including production of antibodies and activation of T cell lymphocytes.

An example for isolation of an inflammatory region can be found in Streptococci that trigger the induction of neutrophils that secrete mainly hyperperoxides. The response to the bacteria may among other effects preclude blood supply to the area and forms three radiuses: pus, inflammation and isolation. As the infection propagates, immune complexes may be released to the blood stream and cause a sepsis cascade. In immunotherapy, this may increase danger that the tumor may enter a necrotic, rather than apoptotic, procedure, causing sepsis. Therefore, the desired cascade is tumor elimination through an apoptotic procedure, rather than necrosis.

The inflammation response has three roles: 1. Transfer of molecules and cells to the infected region aimed at killing/eliminating the invader; 2. Formation of a finite border to prevent the spread of the infecting agent; 3. Fix damaged tissue.

Three processes take place at the inflammation site: 1. Enlargement of blood vessels and elevation in blood flow; 2. Expression of molecules that bind leukocytes; 3. Elevation in permeability of blood vessels, enabling migration of leukocytes. These processes are influenced by release of prostaglandins, leukotrienes, platelet activating factors followed by cytokines and chemokines by macrophages.

Monoclonal antibodies are able to target a single specific protein on cancer cells while minimizing collateral damage to healthy tissue that is caused by the toxicity associated with chemotherapy and radiation therapy. Since scientists were able to create monoclonal antibodies that could be safely used in humans, eight monoclonal antibodies have been approved for use in clinical treatments to trigger immune responses to cancer cells, modulate cancer cell growth, and deliver drugs to cancer cells. Of these, only three are used on solid tumors (85% of all cancers).

A major difficulty in developing monoclonal antibody treatments for solid tumors relates to their ability to penetrate the tumor. To be effective, the treatment must gain access to many viable cells within tumors at sufficient concentrations to effect a maximal change in the tumor. This is affected by several factors, including the characteristics of the tumor, the antibody, and the target. Recently, it has been shown that boosting the immune killer cells, it is possible to increase the antibody effectiveness against the tumor. T. Sato and K. Hasumi reported (Apr. 18, 2007, Annual Meeting of the American Association for Cancer Research in Los Angeles) that they were able to show in laboratory studies that adding NK cells expanded outside the body to a monoclonal antibody, Herceptin, which targets the HER2/neu protein on breast cancer cells, was more efficient at killing the cancer cells.

SUMMARY OF THE INVENTION

In one aspect, the present invention provides microparticles or nanoparticles for treatment of tumors comprising:
(i) a targeting agent to the tumor or the tumor environment; and
(ii) at least one inducer that stimulates a desired immune response in the tumor environment, leading to tumor apoptosis,
wherein components (i) and (ii) are non-covalently or covalently attached to the surface of said microparticles or nanoparticles.

According to this aspect, the invention further provides pharmaceutical compositions comprising said microparticles or nanoparticles and a method for treatment of tumors comprising administering to a patient in need said pharmaceutical composition or said microparticles or nanoparticles.

In another aspect, the invention provides a kit for treatment of malignant tumors comprising:

(i) a composition comprising microparticles or nanoparticles carrying a targeting agent to the tumor or the tumor environment and an agent A, which is a member of a pair of agents A-B that bind with high affinity to each other;

(ii) a composition comprising microparticles or nanoparticles carrying at least one inducer that stimulates a desired immune response in the tumor environment and the agent B of said pair of agents A-B; and (iii) a leaflet with instructions for administration of composition (i) before composition (ii), wherein the components of each of the compositions (i) and (ii) are non-covalently or covalently attached to the surface of said microparticles or nanoparticles.

In a further aspect, the invention provides a kit for treatment of malignant tumors comprising:

(i) a composition comprising microparticles or nanoparticles carrying a targeting agent to the tumor or the tumor environment and an agent A, which is a member of a pair of agents A-B that bind with high affinity to each other;

(ii) a composition comprising microparticles or nanoparticles carrying the agent B of said pair of agents A-B, and an agent C, which is a member of a pair of agents C-D that bind with high affinity to each other;

(iii) a composition comprising microparticles or nanoparticles carrying the agent D of said pair of agents C-D; and (iv) a leaflet with instructions for administration of sequential administration of compositions (i), (ii) and (iii), respectively, wherein the components of each of the compositions (i), (ii) and (iii) are non-covalently or covalently attached to the surface of said microparticles or nanoparticles.

BRIEF DESCRIPTION OF THE FIGURES

The patent or application file contains at least one drawing executed in color. Copies of this patent or patent application publication with color drawings will be provided by the Office upon request and payment of the necessary fee.

Cells incubated with uncoated Avidin beads. Red arrows show the beads, blue arrows show THP-1 cells.

Figure 9A:
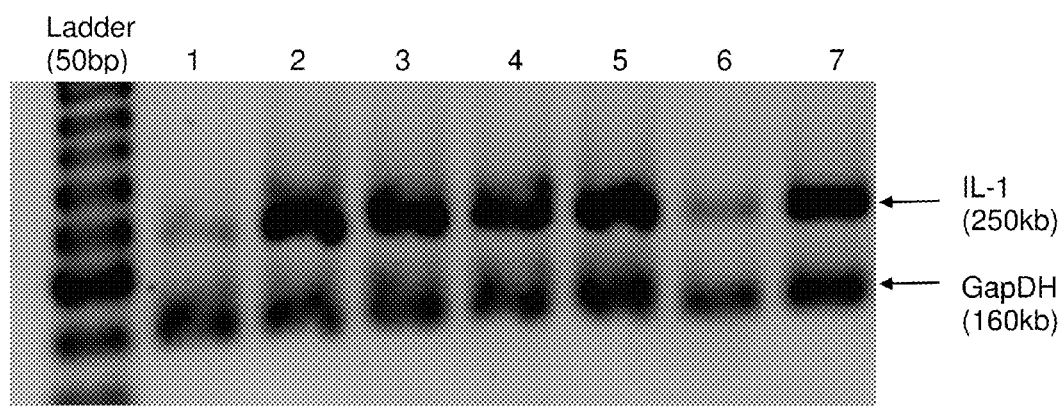
Figure 9B:
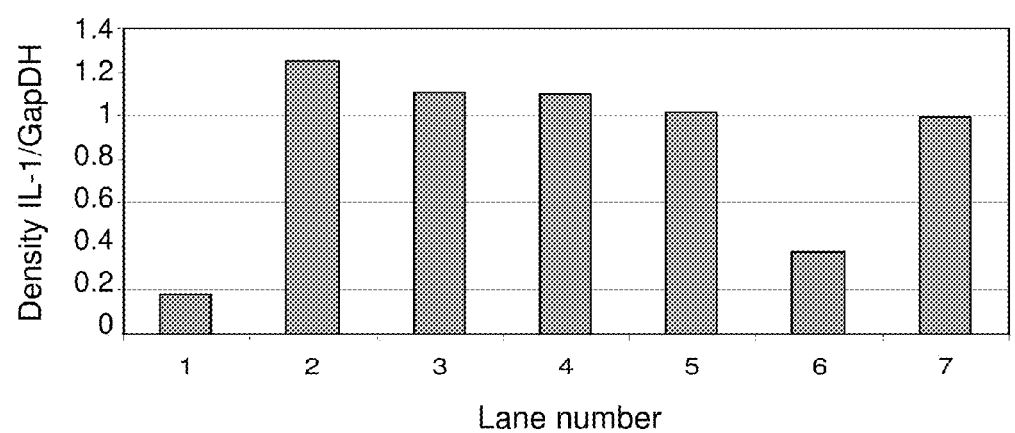
Figure 10A:
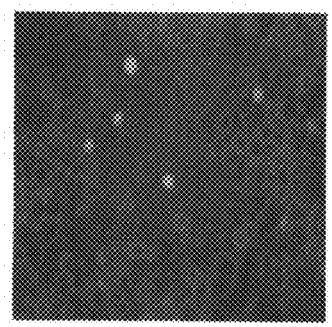
Figure 10B:
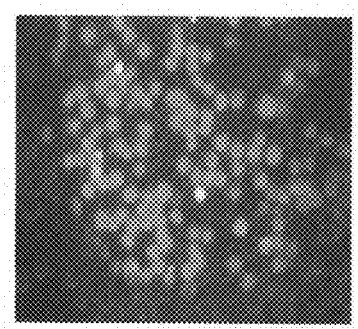
Figure 10C:
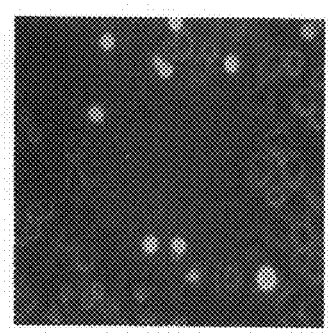
Figure 10D:
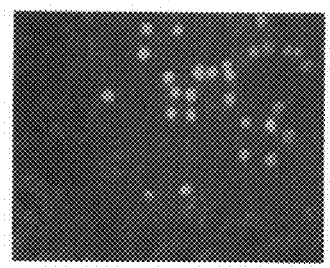
Figure 10E:
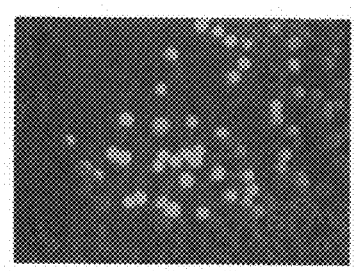
Figure 10F:
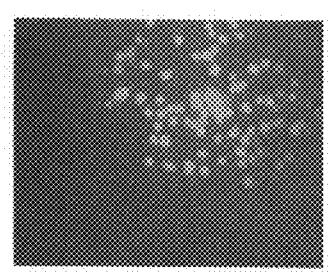
Figure 10G:
Figure 10H:
Figure 10I:
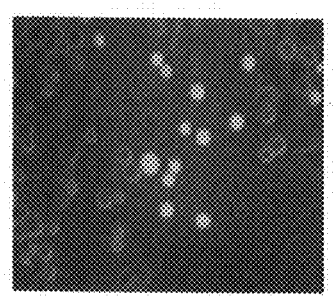

FIGS. 9A-9B show induction of IL-1 transcription in THP-1 monocytes by Biomag™ particles carrying anti-HER2 Abs and LPS. (A) Image of 2.3% electrophoresised agarose gel for IL-1 (250 bp) and GapDH (160 bp) RT-PCR products from THP-1 incubation with Biomag™. (B) Densitometry analysis graph of average pixel density from gel imaging (Quantity one pixel analysis) Lanes represent PCR products of THP-1 cells incubated with Biomag™ carrying: (1) Cells only (negative control); (2) Soluble LPS (positive control); (3) Biot-LPS; (4) 25% Biot-anti HER2 and 75% Biot-LPS; (5) 50% Biot-anti HER2 and 50% Biot-LPS; (6) Biot-anti HER2; (7) 75% Biot-anti HER2 and 25% Biot-LPS.

Figs. 10A-10I show that Biomag™ particles carrying anti-HER2 Abs and LPS mediate attachment of THP-1 monocytes (stained with CFSE) to SK-BR-3 cells. (A) No Biomag™. Cells were incubated with irrelevant Ab's (negative control); (B) No Biomag™. Cells were incubated with soluble anti HER2 (positive control); (C) No Biomag™. Cells were incubated with soluble LPS; (D) Cells incubated with Biomag™ carrying Biot-LPS; (E) Cells incubated with Biomag™ carrying Biot-anti HER2; (F) Cells incubated with Biomag™ carrying 25% Biot-anti HER2 and 75% Biot-LPS; (G) Cells incubated with Biomag™ carrying 75% Biot-anti HER2 and 25% Biot-LPS; (H) Cells incubated with Biomag™ carrying 50% Biot-anti HER2 and 50% Biot-LPS; (I) Uncoated cells incubated with Biomag™. Fluorescent CSFE-stained THP-1 cells at high concentrations are seen in samples containing Ab's.

Figure 11B:
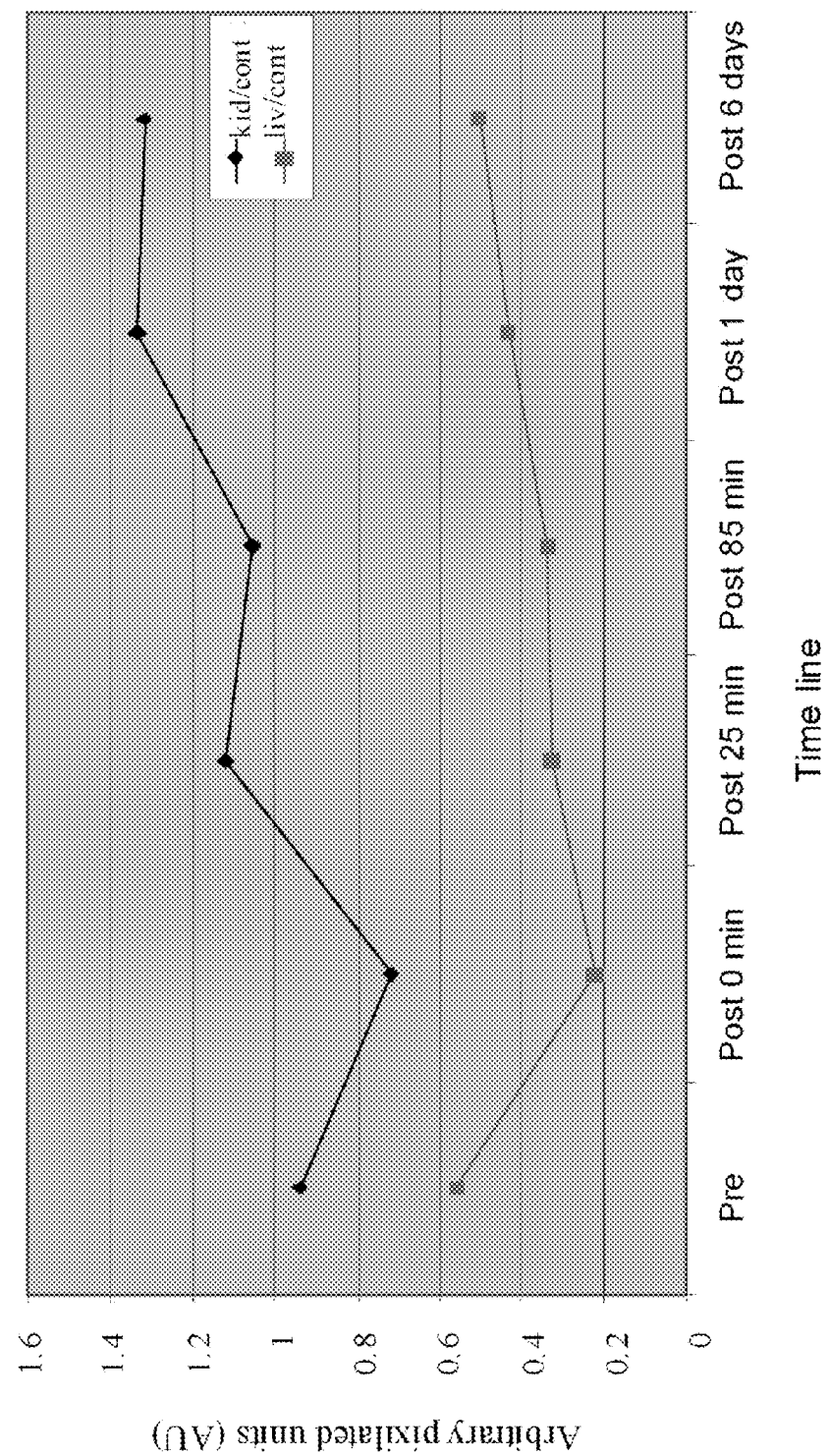

FIGS. 11A-11B show MRI imaging of a mouse treated with Biomag™ particles carrying anti-HER2 Abs and LPS. (A). MRI T2* images of mouse injected i.v with $10^8$ particles of Biomag™ particles carrying anti-HER2 Abs and LPS (10% of bi-LPS bound 90% Ab's) showing particles dispersal in organs. Shown are pretreatment 0, 25 min, 85 min, 1 day and 6 days post treatment. Green, red and yellow margins were used for pixel analysis of particles accumulation and deposits in liver, kidney and unaltered muscle tissue as control, respectively. (B) Pixel analysis of average pixels of all available MRI slices images showing above organs of interest kidney (blue line) and liver (pink line) normalized with the control muscle tissue.

Figure 12:
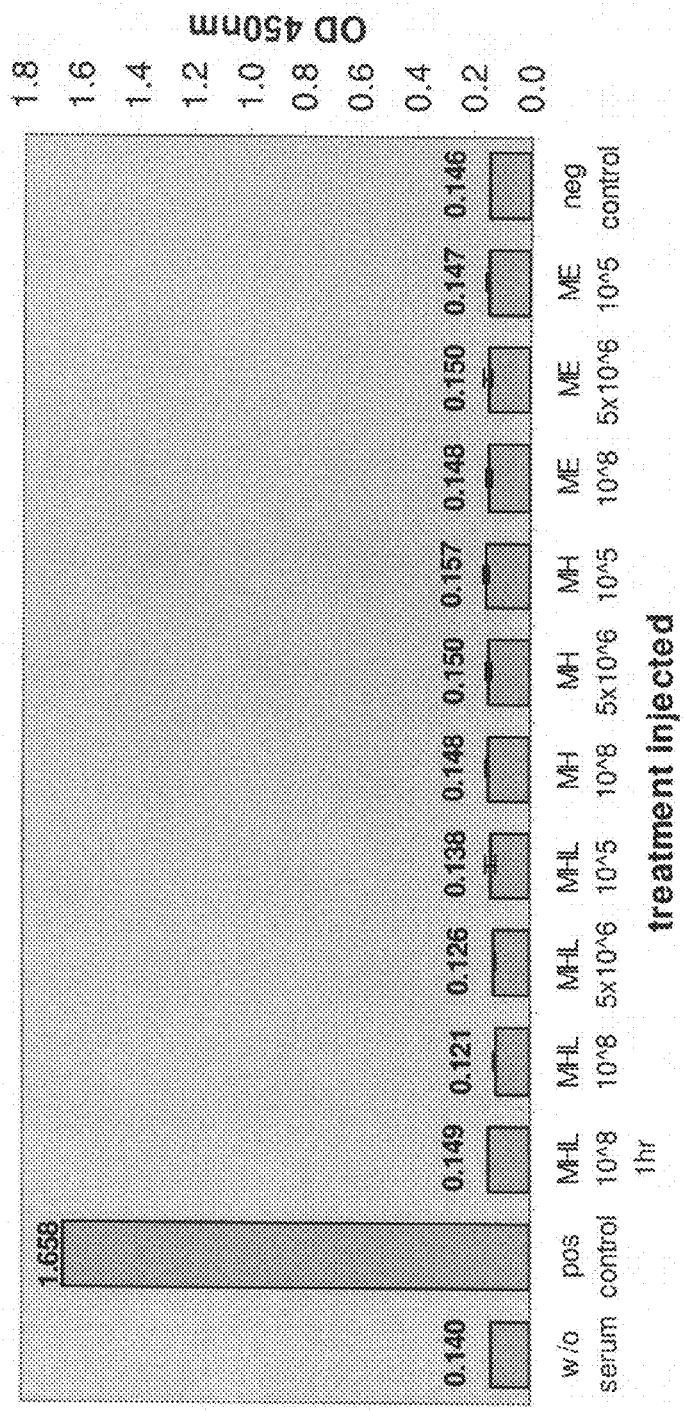

FIG. 12. ELISA demonstrating anti avidin antibody reaction in mice 3 weeks after injection of Biomag™ particles carrying anti-HER2 Abs and LPS. Plates were coated with 100 µl per well of 5 µg/ml avidin dissolved in PBS, blocked with 2% Bovine Serum Albumin (BSA) in PBS for 1 hour, incubated for 1 hour with 1:100 diluted serum from mouse injected as indicated in the Figure (ME, empty particles; MH, particles carrying human anti HER 2 antibody; MHI, particles carrying human anti HER 2 antibody and LPS; positive control, biotin horseradish peroxidase (HRP); negative control, untreated mice). Secondary antibody was goat anti mouse IgG +HRP. Substrate was OPD (o-phenylenediamine dihydrochloride). Between incubations plates were washed 3 times with PBS 0.05% TWEEN 20.

Figure 13:
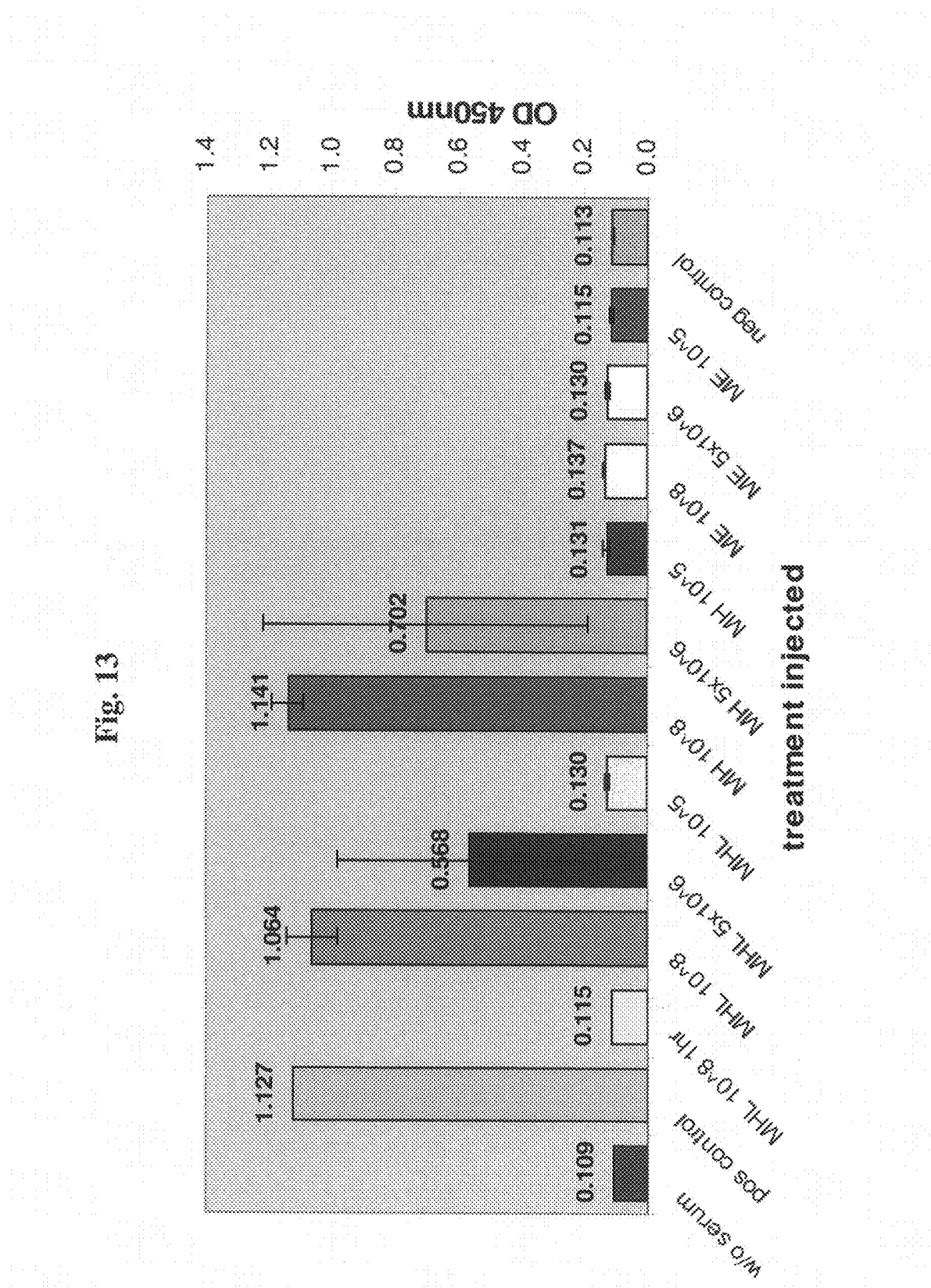

FIG. 13. ELISA demonstrating anti human IgG antibody reaction in mice, 3 weeks after injection of Biomag™ particles carrying anti-HER2 Abs and LPS. Plates were coated with 100 µl per well of 5 µg/ml anti human IgG dissolved in PBS, incubated for 1 hour with 1:100 diluted serum from mouse injected as indicated in the Figure (positive control, goat anti human HRP, negative control, untreated mice). Secondary antibody was goat anti mouse IgG +HRP. Substrate was OPD. Between incubations plates were washed 3 times with PBS 0.05% TWEEN 20.

Figure 14B:
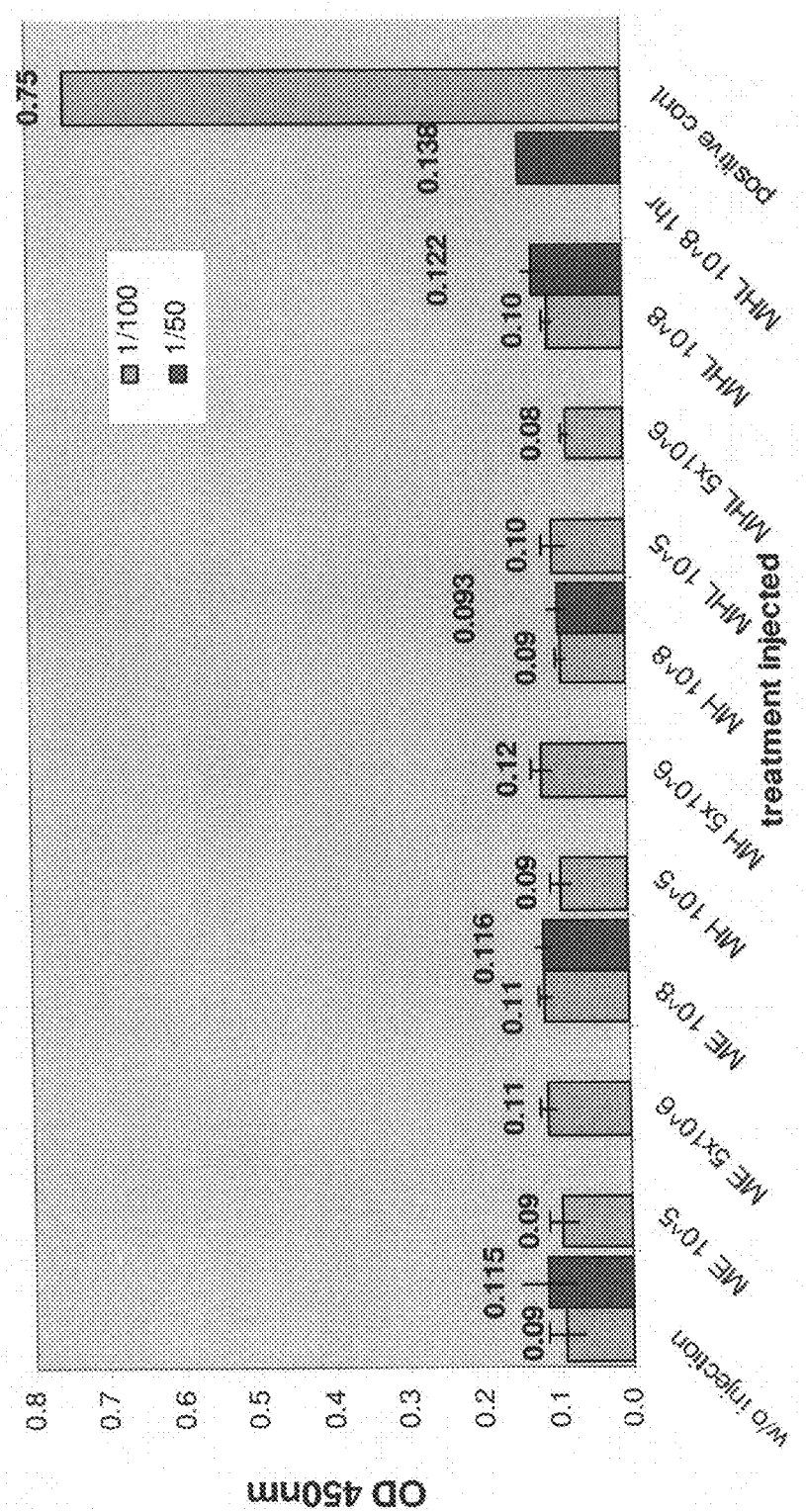

FIGS. 14A-14B ELISA demonstrating anti LPS of 1:5000 blocked with 2% Bovine Serum Albumin (BSA) in PBS for 2 hour, anti LPS humoral reaction in mice 3 weeks after injection with Biomag™ particles carrying anti-HER2 Abs and LPS. Plates were coated with 100 µl per well of (A) LPS (Sigma) or (B) Bi LPS at dilutions incubated 1 hour with 1:50 and 1:100 diluted serums from mouse injections as indicated in the Figure. positive- avidin HRP, negative- untreated mice. Secondary antibody was goat anti mouse IgG +HRP. Substrate was OPD. Between incubations plates were washed 3 times with PBS 0.05% TWEEN 20.

DETAILED DESCRIPTION OF THE INVENTION

In accordance with the present invention, tumor is treated as a foreign body (pathogen or implant) that needs to be rejected by the immune response.

It is an object of the present invention to interrupt the tumor environment in a way that will prevent efficient blood transfer and block normal activity of the tumor. The aim is not the tumor cells, but the whole tumor mass. The purpose of this treatment is to attract cells and molecules to the tumor microenvironment that instigate tumor apoptosis.

In one aspect, the present invention relates to microparticles or nanoparticles for treatment of tumors comprising:
(i) a targeting agent to the tumor or the tumor environment; and
(ii) at least one inducer that stimulates a desired immune response in the tumor environment, leading to tumor apoptosis,
wherein components (i) and (ii) are non-covalently or covalently attached to the surface of said microparticles or nanoparticles.

In another aspect, the present invention relates to a kit for treatment of tumors comprising:
(i) a composition comprising nanoparticles or microparticles carrying a targeting agent to the tumor or the tumor environment and an agent A, which is a member of a pair of agents A-B that bind with high affinity to each other;
(ii) a composition comprising nanoparticles or microparticles carrying an inducer that stimulates a desired immune response in the tumor environment and the agent B of said pair of agents A-B; and
(iii) a leaflet with instructions for administration of composition (i) before composition (ii),
wherein the components of each of the compositions (i) and (ii) are non-covalently or covalently attached to the surface of said microparticles or nanoparticles.

In a further aspect, the present invention relates to a kit for treatment of tumors comprising:
(i) a composition comprising nanoparticles or microparticles carrying a targeting agent to the tumor or the tumor environment and an agent A, which is a member of a pair of agents A-B that bind with high affinity to each other;
(ii) a composition comprising nanoparticles or microparticles carrying the agent B of said pair of agents A-B and an agent C, which is a member of a pair of agents C-D that bind with high affinity to each other; and
(iii) a composition comprising nanoparticles or microparticles carrying the agent D of said pair of agents C-D; and
(iv) a leaflet with instructions for administration of compositions (i), (ii) and (iii) sequentially in this order, at intervals,
wherein the components of each of the compositions (i), (ii) and (iii) are non-covalently or covalently attached to the surface of said microparticles or nanoparticles.

It is also envisaged by the present invention to replicate steps (ii) and (iii) by providing along with agent D an agent E in composition (iii), wherein E is a member of a pair of agents E-F that bind with high affinity to each other, and a further composition comprising the agent F of the pair of agents E-F. This procedure can be repeated with other pairs of agents G-H, I-J, and so on, as desired. The intention is to accumulate a large number of beads in order to block supply of blood and other factors that support the tumor growth.

As used herein, the term "targeting agent" means an agent that recognizes and binds to an antigen, a receptor or other molecules found on the surface of tumor cells or in the tumor environment. These are antibodies or ligands that recognize molecules that are over-expressed or expressed de-novo on the surface of the tumor cells.

Examples of targeting agents include, without being limited to: (i) an antibody to a tumor-associated antigen (TAA) or to a peptide of such TAA antigen such as HER 2, CD20, CD22, CD33 or CD52, or the cancerous form of MUC1 mucin peptide; (ii) an antibody to a receptor associated with cancer found on the surface of cancer cells such as epidermal growth factor receptor (EGFR); (iii) an antibody to vascular endothelial growth factor (VEGF), an antigen associated with angiogenesis in the tumor environment; and (iv) a ligand to a receptor found on the surface of tumor cells such as ganglioside GM-1 and GM-2, which ligands are E. coli enterotoxin (LT) and cholera toxin (CT), respectively. MUC1 mucin is a breast cancer-associated transmembrane glycoprotein, of which the extracellular domain is formed by a repeating 20-amino acid sequence. The cancerous form of MUC1 differs from the normal form by glycosylation quantity and quality and by number of the repeats of the outer membrane 20 amino acids; antibodies can be raised against three repeats of the of the cancerous form of MUC1 mucin 20-amino acid peptide.

The targeting agent is preferably an antibody, preferably a monoclonal antibody (mAb), more preferably, a chimeric, human or humanized mAb, specific to an antigen found on the tumor cells (tumor associated antigen, TAA) or on the environment of the tumor. Any known mAb presently in use or being tested clinically or to be developed in the future for cancer therapy can be used according to the invention. Examples of mAbs that can be used according to the invention include, without being limited to: Alemtuzumab, an anti-CD52 mAb (trade name Campath-1H), used as a treatment for B-cell chronic lymphocytic leukaemia (CLL) and multiple sclerosis; Bevacizumab, a humanized anti-VEGF mAb (trade name Avastin), approved for inhibition of angiogenesis and useful for treatment of colorectal cancer and other types of cancer; Cetuximab, a chimeric murine-human anti-EGFR mAb (trade name Erbitux), used for treatment of colorectal cancer; Edrecolomab, a chimeric mouse/human mAb to the cell surface glycoprotein EpCAM (17-1A) expressed on epithelial tissues and on various carcinomas (trade name Panorex); Epratuzumab, a humanized antihuman CD22 IgG1 antibody, useful for treatment of non-Hodgkin's lymphomas; Gemtuzumab, an anti-CD33 mAb (trade name Mylotarg®), approved for treatment of some types of acute myeloid leukaemia (AML). Ibritumomab, an anti-CD20 mAb (trade name Zevalin), useful for treatment of B-cell non-Hodgkins lymphoma; Panitumumab, an anti-EGFR recombinant, human IgG2 kappa mAb (trade name Vectibix), useful for treatment of metastatic colorectal cancer; Rituximab, an anti-CD20 antibody, useful for treatment of B-cell non-Hodgkins lymphoma, B-cell leukemias and some autoimmune diseases, e.g., rheumatoid arthritis; Tositumomab, an anti-CD20 antibody (trade name Bexxar), useful for treatment of B-cell non-Hodgkins lymphoma; Trastuzumab, an anti-HER2/neu mAb (trade name Herceptin), used for treatment of breast cancer; R1507, a human mAb that targets IGF-1R (insulin-like growth factor receptor), in clinical trials for patients with solid tumors; and anti-MUC1 peptide mAbs, useful for treatment of tumors.

In one preferred embodiment, the mAb is an anti-HER2 for targeting breast cancer cells that overexpress HER-2 receptor, that are present in 30% of breast cancer patients, such as the humanized mAb Trastuzumab (trade name Herceptin).

In another embodiment, the targeting agent is a ligand to a receptor found on cancer cells surface such as a LT and CT.

The targeting agent may be optionally biotinylated. In preferred embodiments, the targeting agent is optionally biotinylated anti-HER2 antibody, preferably trastuzumab. The biotinylated targeting agent, e.g., biotinylated trastuzumab is then linked, to avidin- or streptavidin-coated particles carrying the inducer.

The invention further provides a pharmaceutical composition comprising the microparticles or nanoparticles of the invention. The composition may optionally contain a pharmaceutically acceptable carrier and excipients.

The administration of the composition or the compositions of the kit of the invention to a patient will target the particles carrying the targeting agent to the tumor or to its environment and the inducer will stimulate a local response aiming at destruction of tumor mass and its blood supply.

As used herein, the term "inducer" refers to an agent that will induce innate response in the tumor environment leading to tumor damage and apoptosis. The type of response performed by the immune cells attracted to the tumor microenvironment is determined by the inducer that is attached to the particles/beads targeted to the tumor. The inducer determines the cell type to be stimulated and, in some instances, the response elicited by those cells.

Examples of inducers that can be used according to the invention include, without limitation: mannose, mannan, lipopolysaccharide (LPS), a Toll-like Receptor (TLR) ligand, N-formyl-methionyl-leucyl-phenylalanine (fMLF or fMLP), Complement 3a (C3a), Complement 5a (C5a), and a C, CC, CXC or $CX_3C$ chemokine.

In one embodiment, the inducer is an agent that marks the tumor as a pathogen such as mannose, mannan, LPS, or a TLR ligand. Attachment of a bead carrying these molecules to the tumor may be followed by local inflammation. Neutrophils that are attracted to the local of inflammation lead to inhibition or destruction of the tumors.

In another embodiment, the inducer is an agent that marks the tumor as an implant. For example, following attachment of a bead carrying foreign MHC class I or class II molecules or non-self blood group erythrocytes or antigens, activation of a specific subpopulation of T cells is obtained such as T cells, NKT cells or NK cells.

In another embodiment, the inducer is an agent that mediates chemotaxis such as fMLF, C3a, C5a, or a C, CC, CXC or $CX_3C$ chemokine In one embodiment, a sole inducer is attached to the particles. In another embodiment, a combination of two different inducers is used: a first inducer that is constantly released following the binding of the bead and stimulates chemotaxis, e.g., fMLF, C3a, C5a, or a C, CC, CXC or $CX_3C$ chemokine, and a second inducer that is covalently bound to the bead (and therefore bound to tumor cells) and constantly induces an immune response.

The inducer may be optionally biotinylated. In preferred embodiments, the inducer is optionally biotinylated LPS. The biotinylated inducer, e.g., biotinylated LPS, is then linked to avidin- or streptavidin-coated particles carrying the targeting agent.

It is also envisaged to use in the invention a composition comprising particles carrying a targeting agent, e.g., an anti-tumor antibody, and an antigen for which antibodies already exist in the body, e.g., tetanus toxoid antigen (considering that a great part of the population has once received an anti-tetanus injection) or a non-self blood group (e.g., A antigen to a B blood-type patient), instead of an inducer. This antigen will attract the respective antibodies present in the body to the bead. Following the binding of the particles carrying specific antibodies to the tumor to the target cell in the tumor and the attraction of the body antibodies to the antigen on the bead resulting Fc exposure on bead-bound tumor cells, attracting cells with Fc receptor to the site and an elevated immune response occurs at the tumor microenvironment.

In some preferred embodiments, the inducer is a ligand of a TLR . . . Toll-like receptors (TLRs) are transmembrane receptors that play a key role in the innate immune system. They recognize structurally conserved molecules derived from pathogenic microorganisms and alert the immune system to the presence of microbial infections. Examples of TLR ligands include: ligands to TLR1/2, e.g. tripalmitoylated lipopeptide $Pam_3CSK_4$,OspA, Prin PorB; TLR2 ligands, e.g., diacyl lipopeptides $Pam_2CSK_4$ and $MALP2SK_4$, porins, Zymosan, atypical LPS, Hsp70, Hyaluronan; TLR3 ligand, e.g., poly(I-C)dsRNA; TLA4 ligands, e.g., LPS, flavolipin, taxol, Hsp 70, Hsp 60, oligosaccharides of hyaluronic acid; polysaccharide fragments of heparan sulfate; TLR5 ligand, e.g., Flagelin; TLR7 ligands, e.g., imidazoquinolines (imiquimod, R-848), bropirimine, guanosine analogs; and TLR 9 ligands, e.g. unmethylated CpG DNA, chromatin-Ig complexes. In preferred embodiments, the inducer is a TLR ligand selected from LPS, poly(I-C) dsRNA, flagelin and CpG DNA.

In one more preferred embodiment, the inducer is LPS that induces a response in monocyte/macrophage THP-1 cells.

Examples of pair of agents A-B, C-D, E-F, and so on, that bind with high affinity to each other for use in the present invention include, without being limited to: biotin-avidin and antigen-antibody such as tetanus toxoid (TT) antigen-anti-TT antibody, bovine serum albumin (BSA)-anti-BSA antibody, and the like.

Thus, for example, in one preferred embodiment, the beads of composition (i) of the kit carry the targeting agent and biotin (agent A) and the beads of the second composition (ii) carry the inducer and avidin or streptavidin (agent B). In a more preferred alternative, the microparticles or nanoparticles of (i) carry the biotinylated targeting agent and the microparticles or nanoparticles of (ii) are coated with avidin or streptavidin.

In another embodiment, the beads of composition (i) of the kit carry the targeting agent and an antigen, e.g.,tetanus toxoid (TT) antigen (agent A) and the beads of the second composition (ii) carry the inducer and anti-antigen A antibody, e.g., anti-TT antibody (agent B).This will enable binding of the beads of (ii) to the beads of (i) that were administered before and are already located on the tumor cells or on the tumor environment, marking and intensifying tumor recognition and where the inducer will stimulate the immune response in the tumor environment.

In another aspect of the invention, an inducer is not used. In one embodiment, the beads of composition (i) of the kit carry the targeting agent and a first antigen (agent A of the pair of agents A-B), e.g., TT; the beads of composition (ii) carry the antibody to antigen A, in this case anti-TT antibody (agent B), and an antigen different from A, e.g., BSA (agent C of the pair of agents C-D that bind with high affinity to each other), and the beads of composition (iii) carry an antibody (agent D) to the antigen of (ii), e.g. anti-BSA antibody. This will cause accumulation and aggregation of a great number of beads (that may be of various sizes and compositions) at the tumor microenvironment leading to physical blocking of blood supply and stimulation of the immune response in the tumor environment.

As used herein, the terms "particles" and "beads" are used interchangeably to denote the microparticles and nanoparticles of the invention. They may be preferably biodegradable beads, but also non-biodegradable beads are envisaged by the invention, and may release their content in one time or through slow release at a constant rate.

The particles are preferably particles/beads of micro or nano size of iron oxide or of any suitable polymer such as, but not limited to, synthetic polymers, e.g., polystyrene and copolymers thereof, e.g., styrene/divinylbenzene copolymer, or polymethylmethacrylate, polyvinyltoluene; polyamines; polysaccharides, e.g., chitosan; proteins, e.g., gelatin; and polypeptides. Beads are available at sizes from several nanometers (smaller than virus) up to hundreds of microns (larger than body cells) that can be used as carriers of molecules of interest.

According to the present invention, the size of the beads can be in the range from 5 nm to 100 micron or more. One preferred range is of very small nanoparticles from 5 nm to 50 nm, preferably from 10 to 40 nm, more preferably from 20 to 30 nm. A more preferred size is medium sized microparticles in the range from about 1 µm to about 8 µm, more preferably, 1-2 µm, most preferably 1.5 µm or 2 µm, or 8 µm in diameter, that can be used for systemic administration, for example by infusion. Another more preferable size of microparticles is in the range from about 10 to about 100 µm, preferably 10-50 µm, more preferably, 10-20 µm, most preferably 10 µm. These large microparticles can be used for direct administration to the tumor.

The particles should be on the one hand as small as possible, for example, up to 2 µm, in order to reach all metastases via the blood stream, and on the other hand large enough, for example, up to about 4 micron if carried via blood stream, and up to 100 micron (or even larger) if injected directly to tumor, so as not to be taken up by phagocytes.

According to the invention, the targeting molecule, e.g., an antibody, should bind the cancer cell allowing the inducer molecule, e.g., LPS, to stimulate the desired response for an extended time period. Ideally, a large bead is targeted and attached to tumor cells. The bead releases then the inducer molecules that attract phagocytic cells and stimulate detrimental reactions towards the tumor.

In accordance with the invention, the components may be attached to the beads physically (non-covalently, as in the case of biotin-avidin)) or by conjugation of proteins (antigens, antibodies) to the microbeads via chemically active/ functional groups present on the surface of the beads. The functional groups may be, but are not limited to, amino, hydroxyl, carboxyl, hydrazide, chloromethyl, and the like. Polymeric particles and also polymer coated-iron oxide particles with functional groups are commercially available. The functional groups are activated by standard procedures toward the conjugation. For biotin and biotinylated molecules, avidin- or streptavidin-coated beads are used, which are commercially available or can be made by standard procedures.

The micro- or nano-beads of the invention carrying the anti-tumor antibody and the inducer have the potential to improve existing antibody-based anti-tumor therapy by inducing amplified reactions in solid cancers due to: 1. the targeting of many antibody molecules per bead with elevated affinity and avidity; and 2. the inducer or mixture of inducers, e.g., LPS, complement proteins (e.g. C3a, C5a) attract a variety of cells and responses at the tumor microenvironment.

In preferred embodiments of the invention, the particles are microparticles having a core of iron oxide or polystyrene coated with avidin or streptavidin, the targeting agent is biotinylated humanized anti-HER2 antibody (Trastuzumab), and the inducer is biotinylated LPS.

The quantitative ratio between the targeting agent/antibody and the inducer determines the ability to reach the tumor and stimulate the cells in its environment. This ratio is determined experimentally for each bead/targeting agent/inducer/tumor type. For example, for anti-HER2 mAb and LPS, the suitable ratio may be 9:1 to 1:3 antibody to inducer ratio, since the various ratios were tested and did not show any substantial difference in the targeting effect on breast cancer nor in the production of IL-1 by induced cells (not shown).

The present invention enables specific activity of the innate, non-specific, arm of the immune system. Such a combination of the targeting agent/antibody with an inducer of the innate immune response enables treating the tumor as a foreign body rather than a mass of individual targeted cells to be treated separately by antibodies, T-cytotoxic or NK lymphocytes. Combining the specific immune response (antibodies, T lymphocytes) with the innate arm enables targeting of non-specific cells to the tumor and consequent production of inflammation or rejection response. Using beads carrying antibodies together with stimulating agents may initiate an inflammation response with the desired path in the tumor microenvironment (the desired path is one that does not support tumor development), eliminate its development and enhance identification by lymphocytes to destruct the tumor.

The term "tumor" as used herein refers to any malignant tumor. Preferably it is a solid tumor primary or metastatic tumor of different origins such as, without being limited to, breast, colon, rectal, lung, prostate, bladder, kidney, ovary, melanoma, non-melanoma skin cancers, head and neck, or brain cancer, and connective tissue cancers, e.g., sarcomas, but also non-solid tumors are envisaged by the invention such as different types of leukemias, different types of lymphomas and multiple myeloma.

The invention further relates to a method of treatment of tumors, preferably malignant solid tumors, comprising administering to a patient in need a composition of the invention comprising particles carrying a targeting agent and an inducer.

The dose of the composition to be administered will be determined by the competent physician in accordance with the age, type of cancer, and stage of the disease. Sometimes, a sole treatment may be sufficient; other times, two or more treatments may be necessary.

The invention still further relates to a method for treatment of tumors, preferably malignant solid tumors, comprising administering to a patient in need the compositions (i) and (ii) or (i), (ii) and (iii) of the kits of the invention defined above, sequentially, as described in the leaflet of the kit. The dose of the composition to be administered and the interval of time between the administration of compositions (i) and (ii) or compositions (i), (ii) and (iii) of the kit will be determined by the competent physician in accordance with the age, type of cancer, and stage of the disease.

The compositions of the invention comprise the micro- or nano-particles and a pharmaceutically acceptable carrier and are preferably administered by infusion or by direct injection to the tumor (using large beads), particularly to primary solid tumors.

Among the advantages of the present invention it may be mentioned: (i) it is known that chronic inflammation is one of the major causes of tumor progression and metastasis, but the treatment according to the invention causes inflammation limited to the tumor microenvironment in terms of site, size and duration and does not lead to chronic inflammation; (ii) the treatment may induce anergy of CD8+ cells —the aim is not treatment via cytotoxic cells; (iii) the treatment includes components that mimic pathogenic attack but does not replicate nor expands, and above all, includes a component that attracts the responding cells to the tumor site.

In order to test immune response against the bead in vivo, mice with a tumor that expresses tumor MUC1 or human HER-2 are treated with a bead carrying anti-MUC1 or anti-HER-2 and an inducer, respectively, followed by the tests: rejection of the bead, time to reach the tumor, binding to tumor, stimulation of leukocytes, induction of a local reaction (e.g. inflammation), and rejection of tumor as a whole. Response to the beads and its components is tested by ELISA, MRI, organ histology and pathology (as shown in Example 4 and FIGS. 11-14. Rejection of the tumor as a whole is tested by MRI, CT and tumor histology and pathology.

The invention will be now illustrated by the following non-limiting examples.

EXAMPLES

Example 1

Figure 1:
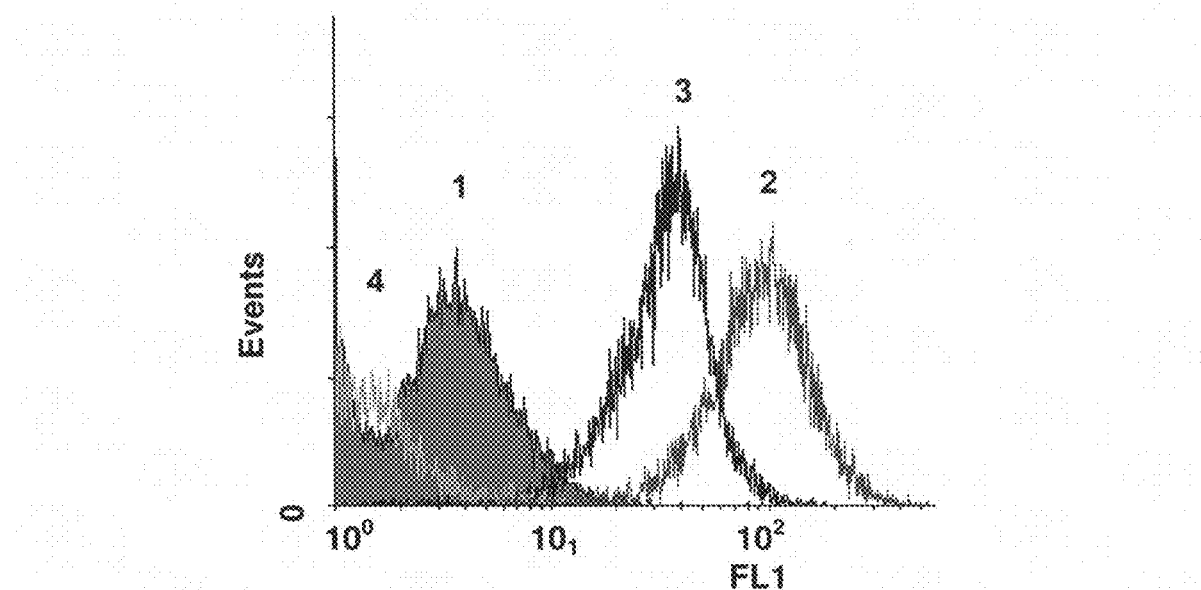
FIG. 1 depicts a FACS histogram demonstrating binding of biotinylated anti-HER2 antibodies (Biot-anti HER2 Ab's) to human breast cancer SK-BR-3 cells (HER2 positive). Monoclonal anti-HER2 Ab's were chemically conjugated to biotin. Biot-anti-HER2 were incubated with SK-BR-3 cells that were stained with streptavidin-FITC (STAVF). Incubated samples were then read by FACS. In the figure: 1 (black-filled red histogram): negative control (nc)—cells incubated only with STAVF; 2 (blue histogram): positive control (pc)—cells incubated with anti-HER2 Ab's stained with goat anti human Fc-FITC Ab's; 3 (black histogram): cells incubated with Biot-anti-HER2 Ab's and stained by STAVF; and 4 (green histogram): cells incubated with Biot not relevant Ab's and stained by STAVF.

Production of Microbeads Carrying Anti-HER2 mAb and LPS (i) Binding of Antibodies to Avidin-coated Beads Monoclonal anti-HER2 antibody (anti-HER2, Herceptin) was biotinylated using the Sulfo-NHS-LC-Biotin kit (Pierce) according to the manufacturer's instructions. Biotinylation rate was determined by HABA test (Acros, USA) according to the manufacturer's instructions. The ability of the biotinylated mAb (Biot-anti-HER2) to detect HER2 was examined by incubation with target cells (SK-BR-3 human breast cancer cells expressing HER2, ATCC) that were stained with STAVF (streptavidin-FITC, Jackson ImmunoResearch). Incubated samples were then examined using Flow Cytometry (FACS). FIG. 1 demonstrates binding of the biotinylated mAb Biot-anti HER2 to SK-BR-3 cells (HER2 positive).

(ii) Biotinylation of Lipopolysaccharide (LPS) [SUPPLIER]

LPS (Sigma L2654) was biotinylated (Biot-LPS) using biotin hydrazide (Pierce) according to the manufacturer's instructions. Biotinylation efficiency was tested by ELISA with avidin and HRP (Jackson ImmunoResearch).

(iii) Binding of Biot-anti-HER2 and LPS to Avidin-coated Microbeads

Figure 2:
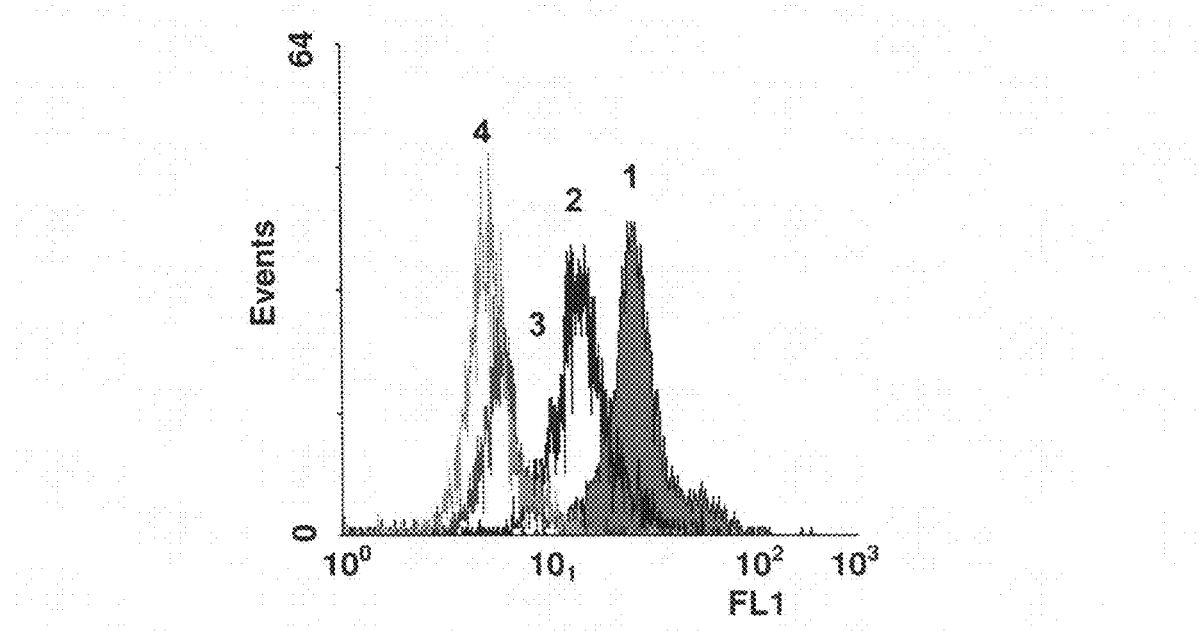
FIG. 2 depicts a FACS histogram demonstrating LPS binding to 8 μm beads. Different volumes of biotinylated LPS (Biot-LPS) were bound to avidin-coated beads, followed by binding of fluorescent Biot-anti-HER2. Samples were fluorescently stained with goat anti human Fc-FITC Ab's. In the figure: 1 (black-filled red histogram): no Biot-LPS bound; 2 (black histogram): 1 μl of Biot-LPS bound; 3 (blue histogram): 5 μl of Biot-LPS bound; and 4 (green histogram): 10 μl of Biot-LPS bound. Reduced fluorescence with increasing volumes of pre-bound Biot-LPS indicates its presence on the beads.

Different mixtures of biotinylated antibody (Biot-anti-HER2) and biotinylated LPS (Biot-LPS) at various desired ratios were prepared, and then bound to avidin-coated microbeads: 2 μm YG polystyrene (Polysciences, USA), 1.5 μm BioMag™, 8 μm magnetic core Compel's beads, 10 μm polystyrene (all from Bangs Laboratories, USA). Samples were fluorescently stained with goat anti human Fc-FITC antibodies (Abs) (Jackson ImmunoResearch). Binding efficiency was examined by FACS. Reduced fluorescence with increasing volumes of pre-bound Biot-LPS indicates its presence on the beads. FIG. 2 demonstrates binding of LPS to the 8 micron magnetic core Compel's beads.

Example 2

Figure 3:
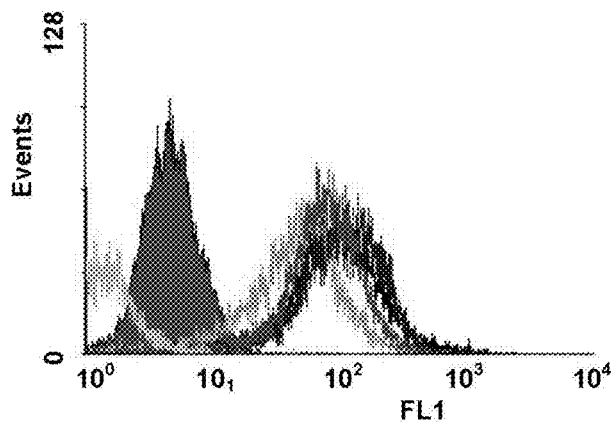
FIG. 3 depicts a FACS histogram demonstrating binding of Biomag™ particles, which are irregularly shaped super paramagnetic particles of an iron oxide core, carrying anti-HER2 Abs and LPS to SK-BR-3 cells. Samples were fluorescently stained with goat anti human Fc-FITC Ab's. 1 (black-filled red histogram): cells incubated with uncoated Biomag™; 2 (black histogram): cells incubated with Biomag™ bound to Biot-anti-HER2 Ab's; 3 (dark blue histogram): cells incubated with Biomag™ bound to 75% Biot-anti-HER2 Ab's and 25% Biot-LPS; 4 (purple histogram): cells incubated with Biomag™ bound to 50% Biot-anti-HER2 Ab's and 50% Biot-LPS; 5 (green histogram): cells incubated with Biomag™ bound to 25% Biot-anti-HER2 Ab's and 75% Biot-LPS; and 6 (light blue histogram): cells incubated with Biomag™ bound to Biot-LPS. Biomag™ particles showed ability to bind the SK-BR-3 target cells when anti-HER2 Ab's were attached. No significant differences in fluorescence were shown between the samples containing Ab's at various ratios with LPS.
Figure 4A:
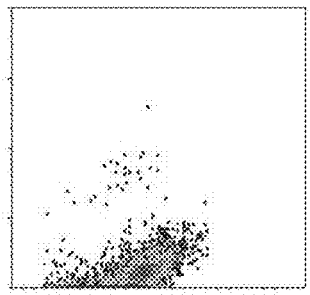
FIGS. 4A-4F present FACS density blots demonstrating ability of Biomag™ particles carrying anti-HER2 Abs and LPS to bind to SK-BR-3 cells. Samples were fluorescently stained with goat anti-human Fc-FITC Ab's. SK-BR-3 cells were incubated with Biomag™ carrying: (A) Biot-LPS (Y-Mean 1.6); (B) Biot-anti-HER2 Ab's (Y-Mean 87.8); (C) 25% Biot-anti-HER2 and 75% Biot-LPS (Y-Mean 41.8); (D) 75% Biot-anti-HER2 Ab's and 25% Biot-LPS (Y-Mean 100.8); (E) 50% Biot-anti-HER2 Ab's and 50% Biot-LPS (Y-Mean 70.3); and (F) Unbound Biomag™ (Y-Mean 4.8). Biomag™ particles showed ability to bind the SK-BR-3 target cells when anti-HER2 Ab's were present. No significant differences in fluorescence were shown between the samples containing Ab's.
Figure 4B:
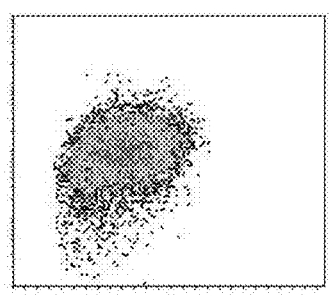
Figure 4C:
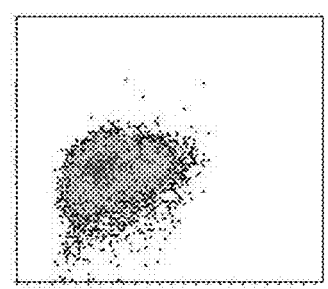
Figure 4D:
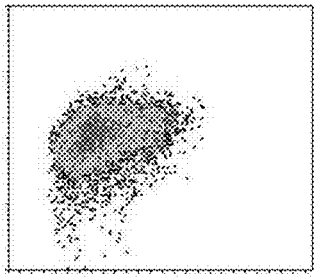
Figure 4E:
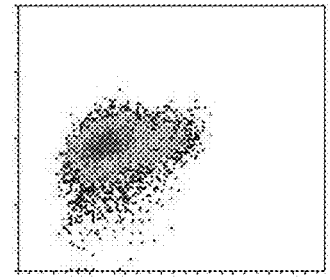
Figure 4F:
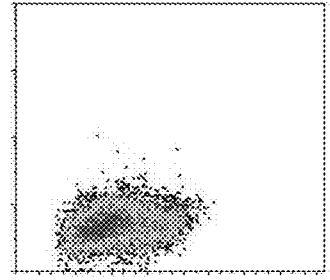
Figure 5A:
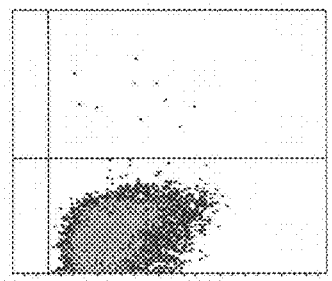
FIGS. 5A-5I depict FACS density blots demonstrating F-Beads binding to SK-BR-3 cells. Blots divided to quadrants, fluorescent cell beads complexes are shown in the upper right quadrant. SK-BR-3 cells were incubated with F-Beads carrying: (A) No beads, negative control (upper right (ur) 0.1%); (B) Cells incubated with soluble anti-HER2 stained with Goat anti human Fc-FITC Ab's, positive control (ur 96.9%); (C) Uncoated, empty beads (1) (ur 1.7%); (D) Biot-LPS, LPS beads (2) (ur 1.7%); (E) Bi Mannose, Mannose beads (3) (ur 1.6%); (F) Biot-anti HER2, Anti HER2 beads (4) (ur 54.5%); (G) Biot-anti HER2 and Biot-LPS, Anti HER2+LPS beads (5) (ur 28.2%); (H) Biot-anti HER2 and Bi Mannose, Anti HER2+Mannose beads (6) (ur 45.9%); and (I) Biot-anti HER2, Biot-LPS and Bi Mannose, Anti HER2+LPS+Mannose beads (7) (ur 8.7%).
Figure 5B:
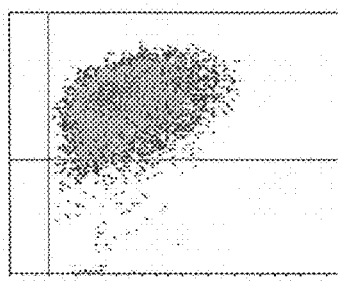
Figure 5C:
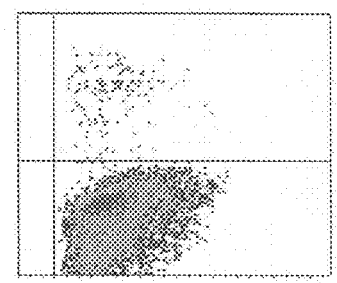
Figure 5D:
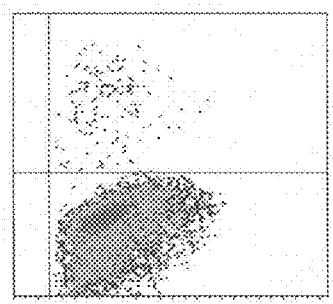
Figure 5E:
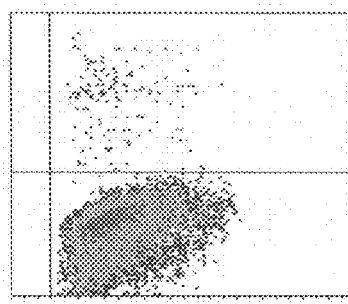
Figure 5F:
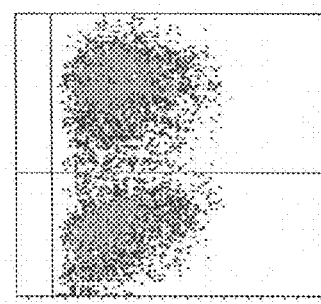
Figure 5G:
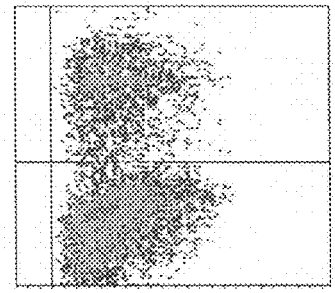
Figure 5H:
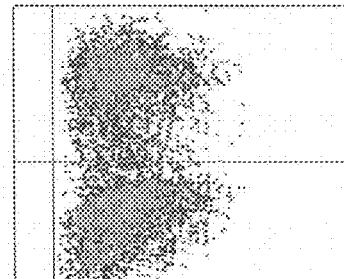
Figure 5I:
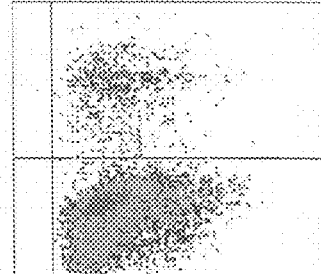
Figure 6A:
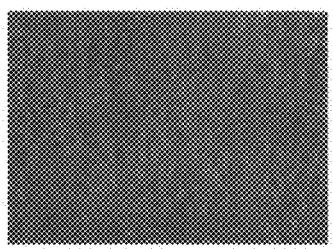
FIGS. 6A-6H show binding of Biomag™ particles carrying anti-HER2 Abs and LPS to SK-BR-3 cells in tissue culture flask. Samples were fluorescently stained with Goat anti-human Fc-FITC. Cells were incubated with Biomag™ carrying: (A) No Biomag™ and irrelevant Ab's; (B) No Biomag™ and soluble anti HER2; (C) Biot-LPS; (D) Biot-anti HER2; (E) 25% Biot-anti HER2 and 75% Biot-LPS; (F) 75% Biot-anti HER2 and 25% Biot-LPS; (G) 50% Biot-anti HER2 and 50% Biot-LPS; and (H) Uncoated Biomag™. Arrows indicate fluorescent dyed Biomag™ bound to cells.
Figure 6B:
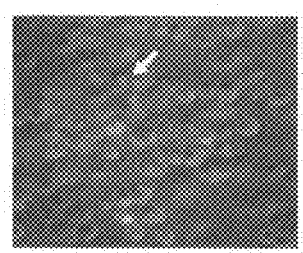
Figure 6C:
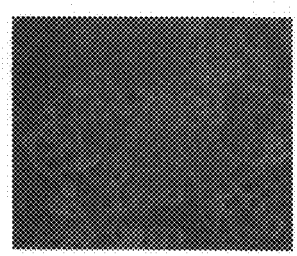
Figure 6D:
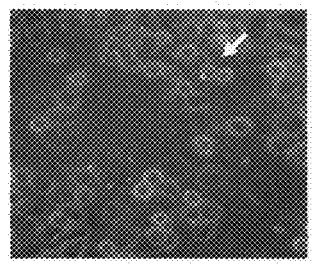
Figure 6E:
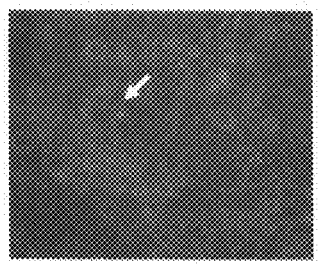
Figure 6F:
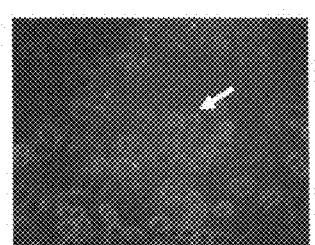
Figure 6G:
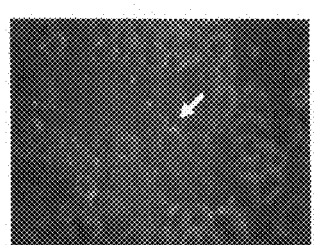
Figure 6H:
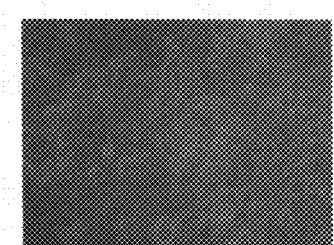

Binding of Microbeads Carrying Anti-HER2 and LPS to SK-BR-3 Cells (a) Mixtures of biot-anti-HER2 and biot-LPS, at various ratios, were attached to fluorescent polystyrene beads 2 µm in diameter (F-Beads) (Fluoresbrite YG Polysciences) or Biomag™ particles (approximately 1.5 µm) (Pierce) covalently coated with avidin, and the beads were incubated with SK-BR-3 cells. Samples were fluorescently stained with goat anti human Fc-FITC Abs and examined by FACS. Both Biomag™ particles (FIGS. 3 and 4) and F-Beads complexes (FIG. 5) demonstrated ability to bind SK-BR-3 target cells when anti-HER2 mAbs were attached to them.

(b) SK-BR-3 cells were incubated overnight in 24-well plates. Biomag™ particles of (a) were added and incubated for one hour, followed by two washes. Samples were fluorescently stained with goat anti-human Fc-FITC for one hour, followed by two washes. Microbeads carrying anti-HER2 mAb and LPS attached to cells were detected by fluorescence microscope. FIG. 6 shows binding of the Biomag™ particles to SK-BR-3 in a tissue culture flask.

Figure 7A:
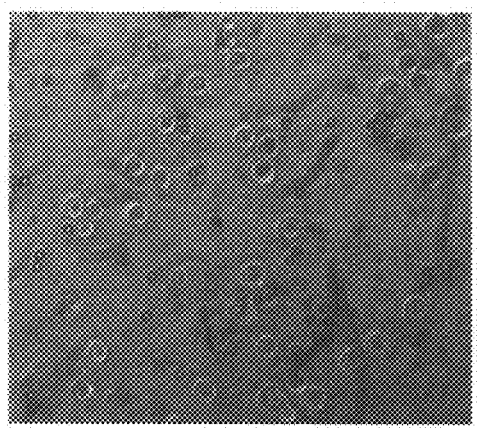
FIGS. 7A-7B show eight-micron beads binding to SK-BR-3 cells. (A) Cells incubated with uncoated Avidin beads; (B) Cells incubated with Avidin Biot-anti HER2. Red arrows show the beads, blue arrows show SK-BR-3 cells.
Figure 7B:
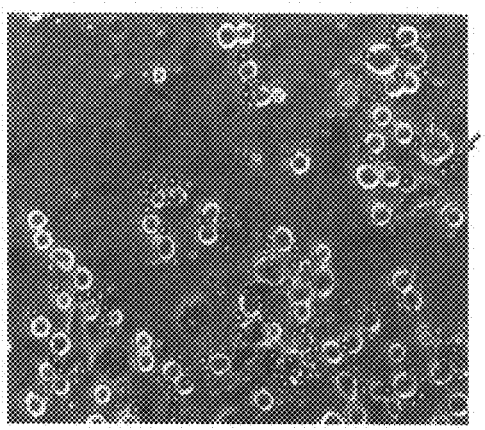

(c) SK-BR-3 cells were incubated overnight in 24-well plates. Eight-micron fluorescent polystyrene beads were added and incubated for one hour, followed by two washes. Attachment of the beads carrying anti-HER2 mAb and LPS to SK-BR-3 cells was detected by fluorescence microscope (FIG. 7).

Example 3

Figure 8A:
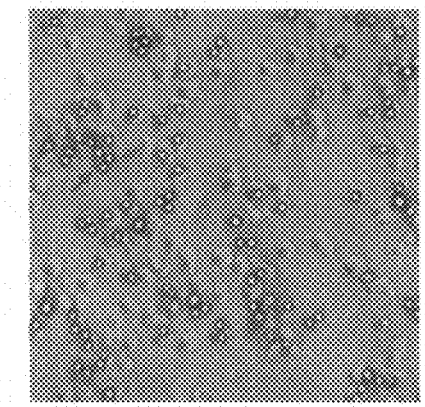
FIGS. 8A-8B show THP-1 monocytes uptake of 10 micron beads. (A) Cells incubated with Avidin Biot-anti HER2. (B)
Figure 8B:
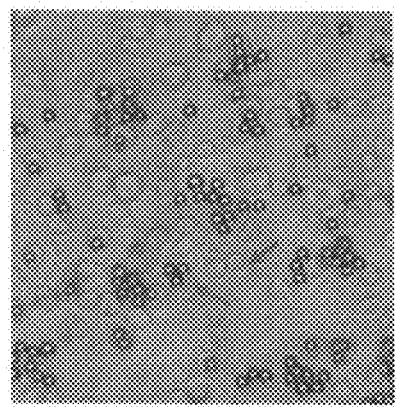

THP-1 Monocytes Response to Beads Carrying Anti-HER2 mAb and LPS (i) Induction of Uptake Human monocytic THP-1 cells (ATCC) were incubated overnight in 24-well plates. Ten-µm polystyrene beads carrying anti-HER2 mAb and LPS particles were added and incubated for 3 hours. FIG. 8 shows the uptake of the 10 µm polystyrene beads by THP-1 monocytes.

(ii) Induction of IL-1 Transcription

THP-1 cells were incubated overnight in 6-well plates. Biomag™ particles carrying anti-HER2 mAb and LPS were added and incubated for 3 hours. Growth medium was discarded. Cells were centrifuged, RNA was extracted using trisol reagent (Sigma). RT-PCR reaction (Promega kit) was performed using Oligo dT primers (Sigma), and the resulted cDNA was used in PCR reaction (Bioline kit) to propagate the IL-1 gene product. The PCR product was run on agarose gel and compared to GAPDH (glyceraldehyde-3-phosphate dehydrogenase, a constitutively expressed gene). DNA was stained with ethidium bromide. Analysis of PCR and comparison among treatments as related to GapDH was performed using Quantity One software (BioRad). The results for IL-1 average density were normalized by dividing with GapDH average density. Significant increase in IL-1 transcription is demonstrated when LPS is present on Biomag™ (FIG. 9).

(iii) Attachment of THP-1 Monocytes to SK-BR-3 Cancer Cells as Mediated by Particles Carrying Anti-HER2 mAb and LPS SK-BR-3 cells were incubated overnight in 24-well plates. Biomag™ particles carrying anti-HER2 mAb and LPS were added and incubated for one hour, followed by 3 washes. THP-1 cells, stained with CFSE fluorescence dye, were added, and allowed to incubate for 3 hours, followed by 3 washes. FIG. 10 shows that Biomag™ particles carrying anti-HER2 mAb and LPS mediate attachment of THP-1 monocytes (stained with CFSE) to SK-BR-3 cells in samples containing anti-HER2 mAb's.

Example 4

Testing Particle Toxicity, Dispersal and Accumulation in Mice Organs

Thirty BALBc mice (8-week old, 25 g weight; Haddasah, Jerusalem) in 10 groups were injected intravenously with Biomag™ particles $10^5$, $5 \times 10^6$ and $10^8$ particles per animal in 100 µl PBS. The particles were injected in three compositions 1. LPS and anti HER2 antibodies (MHL); 2. anti HER2 antibodies (MH); 3. empty particles as control (ME).

A mouse was placed in the MRI imager (BioSpect 4.7/40, 4.7 Tesla Bruker Colorado, operating system pv-4, analysis in-house software written in Interactive Data Language) and injected with high dosage MHL using catheter under sedation. T2* imaging was performed before injection, immediately after injection, 25 minutes, 85 minutes, 1 and 6 days after injection. The results are depicted in FIGS. 11A-11B. The particles migrate and accumulate in liver and kidney immediately after administration. After 6 days, the particles were cleared from liver and kidney Animals were monitored for behavior and weight loss for 1 month and then sacrificed. Blood was taken before sacrifice and serum was isolated. Sera were analysed by ELISA for anti-avidin (FIG. 12), anti-human IgG (FIG. 13) and anti-LPS (FIG. 14) to test antibody response against particle components. No antibody response was detected against avidin or LPS. High immune response was found in mice against the humanized anti-HER2 antibody (Herceptin), which is not relevant in case of human treatment with these beads.

The invention claimed is:

1. Microparticles or nanoparticles for treatment of tumors comprising:
    a microparticulate or nanoparticulate core and, non-covalently or covalently attached to the surface thereof, the following components—
    (i) a targeting agent to the tumor or the tumor environment, optionally biotinylated, selected from the group consisting of: (a) an antibody to a tumor-associated antigen or to a peptide of such an antigen found on the surface of tumor cells; (b) an antibody to a receptor found on the surface of tumor cells; (c) an antibody to an antigen in the tumor environment; and (d) a ligand to a receptor found on the surface of tumor cells, wherein said antibody of (a), (b) or (c) is a chimeric, human or humanized mAb; and
    (ii) two or more inducers optionally biotinylated, that stimulates an innate immune response in the tumor environment, leading to tumor apoptosis, selected from the group consisting of mannose, mannan, lipopolysaccharide (LPS), a Toll-like Receptor (TLR) ligand, N-formyl-methionyl-leucyl-phenylalanine (fMLF or fMLP), Complement 3a (C3a), Complement 5a (C5a), and a C, CC, CXC or $CX_3C$ chemokine.

2. The microparticles or nanoparticles according to claim 1, wherein said monoclonal antibody is selected from the group consisting of Alemtuzumab, Bevacizumab, Cetuximab, Edrecolomab, Epratuzumab, Gemtuzumab, Ibritumomab, Panitumumab, Rituximab, Tositumomab, Trastuzumab, and R1507.

3. The microparticles or nanoparticles according to claim 1, wherein said TLR ligand is selected from the group consisting of: (i) a ligand to TLR1/2; (ii) a TLR2 ligand; (iii) a TLR3 ligand; (iv) a TLR4 ligand; (v) a TLR5 ligand; (vi) a TLR7 ligand; and (vii) a TLR 9 ligand.

4. The microparticles or nanoparticles according to claim 1, wherein the two or more inducers are selected from the group consisting of optionally biotinylated LPS, mannose, mannan, or a TLR ligand.

5. The microparticles or nanoparticles according to claim 1, comprising two inducers, wherein the first inducer is constantly released from the said microparticulate or nanoparticulate core and stimulates chemotaxis, and the second inducer is covalently bound to the surface of said microparticulate or nanoparticulate core.

6. The microparticles or nanoparticles according to claim 5, wherein said first inducer is selected from the group consisting of fMLF, C3a, C5a, a C chemokine, a CC chemokine, a CXC chemokine and a $CX_3C$ chemokine.

7. The microparticles or nanoparticles according to claim 1, wherein said microparticulate or nanoparticulate core is composed of an iron oxide, a synthetic polymer, a polysaccharide, or a protein, has a size from about 5 nm to about 100 micron, may be biodegradable, and may be coated with avidin or streptavidin for binding to biotinylated targeting agents or inducers, or have functional groups on the surface for covalent binding with targeting agents or inducers.

8. The microparticles or nanoparticles according to claim 7, wherein the core is microparticles of the synthetic polymer, polystyrene, or iron oxide coated with avidin and wherein the attached targeting agent is biotinylated anti-HER2 monoclonal antibody and the attached inducer is biotinylated LPS.

9. The microparticles or nanoparticles according to claim 7, wherein said synthetic polymer is polystyrene.

10. A pharmaceutical composition for treatment of tumors comprising microparticles or nanoparticles according to claim 1.

11. The microparticles or nanoparticles of claim 1, wherein the synthetic polymer is selected from the group consisting of polystyrene and copolymers thereof, polymethylmethacrylate, polyvinyltoluene, and polyamines.

12. A kit for treatment of malignant tumors comprising:
(i) a composition comprising microparticles or nanoparticles having a microparticulate or nanoparticulate core carrying (a) a targeting agent to the tumor or the tumor environment and (b) an agent A, which is a member of a pair of agents A-B that bind with high affinity to each other, wherein said targeting agent is selected from the group consisting of: (A) an antibody to a tumor-associated antigen or to a peptide of such an antigen found on the surface of tumor cells; (B) an antibody to a receptor found on the surface of tumor: (C) an antibody to an antigen in the tumor environment; and (D) a ligand to a receptor found on the surface of tumor cells, wherein said antibody of (A), (B) or (C) is a chimeric, human or humanized mAb;
(ii) a composition comprising microparticles or nanoparticles having a microparticulate or nanoparticulate core carrying (c) two or more inducers that stimulates an innate immune response in the tumor environment, selected from the group consisting of mannose, mannan, lipopolysaccharide (LPS), a Toll-like Receptor (TLR) ligand, N-formyl-methionyl-leucyl-phenylalanine fMLF or fMLP), Complement 3a (C3a), Complement 5a (C5a), and a C, CC, CXC or $CX_3C$ chemokine, and (d) the agent B of said pair of agents A-B; and
(iii) a leaflet with instructions for administration of composition (i) before composition (ii),
wherein the components of each of the compositions (i) and (ii) are non-covalently or covalently attached to the surface of said microparticulate or nanoparticulate cores.

13. The kit according to claim 12, wherein the Toll-like Receptor (TLR) ligand is selected from the group consisting of: (i) a ligand to TLR1/2; (ii) a TLR2 ligand; (iii) a TLR3 ligand; (iv) a TLR4 ligand; (v) a TLR5 ligand; (vi) a TLR7 ligand; and (vii) a TLR 9 ligand.

14. The kit according to claim 12, wherein the microparticulate or nanoparticulate cores are composed of an iron oxide, a synthetic polymer, a polysaccharide, or a protein, have a size from about 5 nm to about 100 micron, may be biodegradable, and may be coated with avidin or streptavidin for binding to biotinylated targeting agents or inducers, or have functional groups on the surface for covalent binding with targeting agents or inducers.

15. The kit according to claim 14, wherein said synthetic polymer is polystyrene.

16. The kit according to claim 12, wherein said chimeric, human or humanized monoclonal antibody is biotinylated and is selected from the group consisting of a humanized anti-HER2 mAb, Alemtuzumab, Bevacizumab, Cetuximab, Edrecolomab, Epratuzumab, Gemtuzumab, Ibritumomab, Panitumumab, Rituximab, Tositumomab, and R1507.

17. The kit of claim 12, wherein the synthetic polymer is selected from the group consisting of polystyrene and copolymers thereof, polymethylmethacrylate, polyvinyltoluene, and polyamines.

18. A kit for treatment of malignant tumors comprising:
(i) a composition comprising microparticles or nanoparticles having a microparticulate or nanoparticulate core carrying (a) a targeting agent to the tumor or the tumor environment and (b) an agent A, which is a member of a pair of agents A-B that bind with high affinity to each other, wherein said targeting agent is selected from the group consisting of: (A) an antibody to a tumor-associated antigen or to a peptide of such an antigen found on the surface of tumor cells; (B) an antibody to a receptor found on the surface of tumor cells: (C) an antibody to an antigen in the tumor environment; and (D) a ligand to a receptor found on the surface of tumor cells, wherein said antibody of (A), (B) or (C) is a chimeric, human or humanized mAb;
(ii) a composition comprising microparticles or nanoparticles having a microparticulate or nanoparticulate core carrying (c) the agent B of said pair of agents A-B, and (d) an agent C, which is a member of a pair of agents C-D that bind with high affinity to each other;
(iii) a composition comprising microparticles or nanoparticles having a microparticulate or nanoparticulate core carrying the agent D of said pair of agents C-D; and
(iv) a leaflet with instructions for administration of sequential administration of compositions (i), (ii) and (iii), respectively,
wherein the components of each of the compositions (i), (ii) and (iii) are non-covalently or covalently attached to the surface of said microparticulate or nanoparticulate cores.

19. The kit according to claim 18, wherein each of the pair of agents A-B and C-D that bind with high affinity to each other is different from each other and is selected from biotin-avidin or streptavidin, wherein the biotin is covalently linked to the targeting agent in the microparticles or nanoparticles of composition (i) and the avidin or streptavidin is present as coating of the microparticulate or nanoparticulate core of composition (ii); and an antigen-antibody to said antigen.

20. The kit according to claim 19, wherein said antigen-antibody is selected from the group consisting of tetanus toxoid (TT) antigen—anti-TT antibody and BSA-anti-BSA antibody.

* * * * *